United States Patent [19]

Pouletty et al.

[11] Patent Number: 5,256,541
[45] Date of Patent: Oct. 26, 1993

[54] DETECTION OF SOLUBLE ALLOANTIGEN IMMUNE COMPLEXES

[75] Inventors: Philippe J. Pouletty, Atherton; Chin-Hai Chang, Los Altos, both of Calif.

[73] Assignee: SangStat Medical Corporation, Menlo Park, Calif.

[21] Appl. No.: 788,488

[22] Filed: Nov. 6, 1991

[51] Int. Cl.$^5$ ............... G01N 33/539; G01N 33/543; G01N 33/564
[52] U.S. Cl. ................... 425/7.24; 435/7.94; 436/507; 436/518; 436/539
[58] Field of Search ............... 436/506, 507, 539, 578; 435/7.21, 7.24, 7.25, 7.94

[56] References Cited

U.S. PATENT DOCUMENTS 4,681,782 7/1987 Ozkan .................................. 428/36
4,810,632 3/1989 McMillan .............................. 435/7

OTHER PUBLICATIONS

Y. Iwaki, et al., (1988) Clinical Transplantation 2:81–84. Successful transplants across T warm–positive cross-matches due to IgM antibodies.
Grosse-Wilde and Doxiadis (1989) J. Immunogenetics 16:149–155. Allotyping for HLA Class I using plasma as antigen source.
F. Stevenson, et al. (1986) J. Imm. Methods 86:187–190. Analysis of soluble HLA Class II antigenic material in patients with immunological disease using monoclonal antibodies.
D. Talbot, et al. (1988) J. Imm. Methods 112:279–283. Rapid detection of low levels of donor specific IgG by flow cytometry with single and dual colour fluorescence in renal transplantation.
R. Duquesnoy, et al. (1990) Transplantation 50:427–437. Multiscreen serum analysis of highly sensitized renal dialysis patients of antibodies toward public and private Class I HLA determinants.
S. Martin, et al. (1987) Transplantation 50:427–437. Posttransplant antidonor lymphocytotoxic antibody production in relation to graft outcome.
R. Tsuji, et al., (1985) Tokai J. Exp. Clin. Med. 10:169–174. Biological significance of Ss (serum soluble) HLA-Class I antigens in bone marrow transplantation.
R. Fauchet, et al., (1989) Transplantaiton 30:114–129. Occurance and specificity of anti-B lymphocyte antibodies in renal allograft recipients.
H. Davies, et al. (1989) Transplantation 47:524–527. Soluble HLA antigens in the circulation of liver graft recipients.
Doxiadis and Grosse-Wide (1989) Vox Sang 56:196–199. Typing for HLA Class I gene products using plasma as source.

Primary Examiner—David Saunders
Attorney, Agent, or Firm—Bertram I. Rowland

[57] ABSTRACT

Reactivity between alloantigen and alloantigen-specific ligand, such as HLA and anti-HLA antibody, is detectable in a sample by separating from the sample a portion of a targeted class of ligands (including such ligands complexed with alloantigen) and measuring the amount of alloantigen in such complex containing fractions. In another embodiment of the invention, reactivity between a plurality of samples is detected by measuring soluble alloantigen in at least first and second biological samples and in a mixture of the samples. Since the formation of alloantigen immune-complexes in the mixture alters the physical and immunological behavior of soluble alloantigen, a divergence between the measured and expected concentration of the mixture indicates reactivity.

5 Claims, No Drawings

DETECTION OF SOLUBLE ALLOANTIGEN IMMUNE COMPLEXES

INTRODUCTION

1. Technical Field

The field of this invention is the detection of reactivity between alloantigen and alloantigen-specific ligand in biological samples.

2. Background

In many transplantation-type situations, there is concern for differences between the allotype, especially the HLA type, of a cell source and the cell recipient. In situations where allogenic cells or tissue are taken from a donor and introduced into a recipient, it is desirable that the donor and recipient be as closely HLA matched as possible. The presence in the patient serum of antibodies against HLA antigens of the donor (donor specific crossmatch) or against a high percentage of HLA alleles (PRA testing) predicts a high risk of graft rejection.

The determination of HLA phenotype (HLA typing) is useful in numerous situations such as transplantation, platelet transfusion and forensic or paternity testing. The standard technique for HLA typing and detection of anti-HLA antibodies is microlymphotoxicity, where serum containing antibodies is incubated with HLA antigen-expressing lymphocytes, then with complement. The level of cytotoxicity is then estimated by discriminating between dead and viable cells using various dyes. This method has numerous disadvantages: it is labor intensive; time consuming; requires isolation of cells; requires viable cells; is nonspecific for HLA; and requires a subjective evaluation. Flow cytometry may also be used but requires a large number of cells and expensive instrumentation. do not share the shortcomings described above, and provide a readily discernible result which is significant for the prognosis of graft acceptance.

3. Relevant Literature

References of interest include Duquesnoy et al. (1990) Transplantation 50: 427-37; Martin et al. (1987) Transplantation 44: 50-53; Grosse-Wilde et al. (1989) J. Immunogenet. 16: 149-55; Doxiadis et al. (1969) 59: 449-54; Doxiadis and Grosse-Wilde (1989) Vox Sang 56: 196-99; Davies et al. (1989) Transplantation 47: 524-27; Tsuji et al. (1985) Tokai J. Exp. Clin. Med. 10: 169-74; Stevenson et al. (1986) J. Immunol. Methods 86: 187-90; Fauchet et al. (1989) Transplantation 30: 114-129; Talbot et al. (1988) J. lmmunol Methods 112: 279-83; Iwaki et al. (1988) Clin. Transplantation 2: 81-84.

SUMMARY OF THE INVENTION

Methods and compositions are provided for detecting reactivity between alloantigen and alloantigen-specific ligands in biological samples.

In one embodiment reactivity between alloantigen and alloantigen-specific ligand is detected in a sample by first separating from the sample a portion of a targeted class of ligand (including alloantigen-specific ligand with bound alloantigen). The amount of alloantigen measured generally by conventional immunoassay—in this fraction is found to correlate with the presence of alloantigen-specific ligand in the original sample.

In another embodiment, reactivity between an alloantigen and an alloantigen-specific ligand is detected in a mixture of biological samples by measuring soluble alloantigen concentration in each of first and second samples, and in a mixture of the first and second samples. Soluble alloantigen concentration measurements may be performed by conventional immunoassay. An average of the soluble alloantigen concentration of the first and second samples is used to determine an expected concentration for the mixture. A difference between this expected concentration and the measured soluble alloantigen concentration of the mixture indicates reactivity between the alloantigen and the alloantigen-specific ligand in the mixture.

DESCRIPTION OF THE SPECIFIC EMBODIMENTS

Reactivity between an alloantigen and an alloantigen-specific ligand is indicative of immunological reactivity between two biological samples. Embodiments of this invention find use in identifying antibodies to known histocompatibility antigens (crossmatching), identifying histocompatibility antigens with antibodies of known specificities (tissue typing), identifying general alloreactivity toward a panel of histocompatibility antigens (Panel Reactive Antibody testing, PRA), and monitoring immune complex formation in post-graft situations. A significant advantage of the present invention over the direct detection of alloantigen-specific antibodies is that the amount of non-specific antibody does not affect measurements. Accordingly, the present invention permits the use of undiluted samples and so provides enhanced sensitivity and ease of use over direct antibody measurements.

An alloantigen is a direct or indirect product of an allele which may be detected as an antigen by another member of the same species. The products of such alleles include encoded polypeptides, but also specific polysaccharides and lipids synthesized by allele encoded enzymes. Alloantigens of particular interest in the present invention include histocompatibility antigens, blood group antigens such as the ABO, Lewis group, the endothelial alloantigen system, and the like. Of especial interest are histocompatibility antigens which include major, known as HLA in human, and minor histocompatibility antigen groups.

As used herein, the term ligand represents various classes of binding molecules. Preferred ligands are antibodies. Alloantigen-specific ligands are molecules which are capable of reacting with, or preferentially associating with, alloantigen. Examples of such ligands include anti-allotypic immunoglobulin or fragments thereof, anti-allotypic T cell receptor or derivatives or fragments thereof, HLA binding peptide, etc. and combinations thereof. Preferably, these ligands associate with alloantigen by non-covalent binding.

Reactivity between alloantigen and alloantigen-specific ligand generally results in the formation of alloantigen-ligand complexes. Further, one or more ligands may associate with one or more alloantigens, though, generally, alloantigen-ligand complexes include at least one molecule of alloantigen or fragment thereof combined with at least one molecule of ligand.

As used herein, soluble alloantigens are those not physically associated with cells or other particulate matter at the time of measurement. Soluble alloantigens may be produced by secretion (e.g. of alternatively spliced message), cleaved or shed from cell surfaces, or other mechanisms such as extraction, enzymatic digestion, etc. Protein, lipid or lipid-bound alloantigens are also considered soluble if not physically associated with cells or particulate matter.

Targeted classes of ligands including such ligands complexed with soluble alloantigen may be at least partially separated from solutions containing such ligands, complexes and soluble alloantigen. In a preferred embodiment, such ligands and complexes may be selectively or preferentially precipitated from a solution which also contains uncomplexed soluble alloantigen. Significantly, the separation is premised upon common characteristics of the ligand class rather than specific binding regions or characteristics of the alloantigen. Where the ligands are antibodies, the separation will preferably be based upon common characteristics of antibodies, such as allotypic regions or constant regions, rather than idiotypic regions or bound antigen. The separated fraction need not contain all or most of the targeted ligand nor need the fraction be substantially free of other sample components except the selected alloantigen unbound to the targeted ligand class. In general, however, the greater the percentage of targeted ligand separated (including alloantigen-specific ligand bound to alloantigen), the greater the sensitivity of the assay.

Suitable precipitating agents include polyethylene glycol, ammonium sulfate, anti-human-Ig antibody, protein A and the like. Of particular interest are polyethylene glycol and ammonium sulfate. The specific conditions employed such as concentration of precipitating agent and incubation time are exemplified below and otherwise known to those skilled in the art.

Samples, as used herein, include biological fluids such as blood, saliva, lymph, dialysis fluid and the like; organ or tissue culture derived fluids; and fluids extracted from physiological tissues. Also included in the term are derivatives and fractions of such fluids. Preferred samples are physiological fluids such as blood or derivatives thereof, serum or plasma (hereafter "blood"), with or without dilution. Where used, dilution will generally be at least 1:10, preferably 1:25, with an appropriate buffered medium, e.g. 0.1 M PBS at pH 7-8. The volume of sample used (diluted or whole) is sufficient to allow for measurable binding of soluble alloantigen to the insoluble receptors.

The term samples also includes the fluids described above to which additional components have been added. For example, in HLA typing, a sample may be a biological fluid to which one or more alloantigen-specific ligands have been added. Examples of other components which may be added to the above described fluids include one or more alloantigens and components which can affect the reactivity between alloantigen and alloantigen-specific ligand. Examples of the latter include components which affect the ionic strength, pH, total protein concentration, etc. In addition, the samples may be treated to achieve at least partial fractionation or concentration. For example, in some embodiments, the assayed samples will have been treated to at least partially remove selected alloantigen.

As used herein, a graft recipient is an individual to whom tissue or cells from another individual (donor), generally of the same species, has been transferred. The graft recipient and donor are generally mammals, preferably human. The stage of development of the recipient will generally range from fetal to adult, preferably from juvenile to adult. The donor may be of any stage of development from embryo to adult. Donor tissue may also be extracted from deceased individuals where the tissue is viable at the time of grafting.

By grafting it is meant that the donor tissue is joined with the graft recipient's body. Preferred grafts include the transplantation of cells, tissues and organs. Of especial interest are the transfusion of blood or blood components, the grafting of bone, skin, bone marrow, etc., and the transplantation of tissues of the eye, pancreas, liver, kidney, heart, brain, bowel, lung, etc. Of greatest interest are transfusions of blood and transplantation of kidneys. Such cells or tissues may be treated between collection and grafting. Pretreatment may include methods of fractionation to isolate or enhance or decrease the concentration of specific cell types, tissue components, compounds, etc.; treatment with detergents or reagents to modify antigen-antibody binding. In addition, donor tissue or cells may be subject to in vitro treatments such as culture, differentiation, proliferation, and genetic manipulation prior to transfer to the recipient.

Measuring the concentration of an alloantigen in a sample or fraction thereof may be accomplished by a variety of specific assays. In a preferred embodiment, a sandwich type assay is used, similar to conventional immunoassays. A sandwich assay is performed by first attaching an otherwise soluble alloantigen specific receptor (henceforth, first receptor) to an insoluble surface or support. The first receptor may be bound to the surface by any convenient means, depending upon the nature of the surface. The particular manner of binding is not crucial so long as it is compatible with the reagents and overall methods of the invention. Where the first receptors are proteins such as antibodies, they may be bound to the plates covalently or non-covalently, preferably non-covalently.

The first receptor may be any compound which binds the alloantigen with sufficient specificity such that the alloantigen can be isolated from other components present in the sample. Several immune molecules with alloantigen binding affinity such as CD4, CD8, and the TCR may provide useful first receptors, either directly or through derivatives thereof. Lectins may be useful where the alloantigen can be selected by the presence of saccharides. Where the alloantigen is a protein or glycoprotein, especially useful first receptors are antibodies against the alloantigen. Instead of whole or intact antibodies, one may use antibody fragments, e.g., Fab, F(ab')$_2$, light or heavy chain fragments, etc. The amount of bound receptor antibody is sufficient to permit detection of subsequently bound soluble alloantigen. Where a specific alloantigen is sought to be detected, the use of affinity purified polyclonal antibodies or monoclonal antibodies is preferred.

In a preferred embodiment of the invention, the first receptors are antibodies specific to one or more HLA alloantigens. Such antibodies may be polyclonal or monoclonal and are generally commercially available or alternatively, readily produced by techniques known to those skilled in the art. For detecting Class II HLA molecules, the antibodies may be specific for either $\alpha$ or $\beta$ chains; for Class I HLA, specificity may be to the MHC gene encoded chain or the associated $\beta$-2 microglobulin chain; or for either Class, specificity may be to a conformational epitope expressed by the combination of both chains. The antibodies may be specific to epitopes conserved across a class of HLA molecules or specific to an epitope expressed by a subset of HLA molecules. Subsets of Class II molecules include products of the DP, DQ and DR gene regions and those of Class I molecules include products of the B, C, and A regions. The antibodies may be directed to a constant region or a portion of the polymorphic region of specific alleles.

The insoluble supports may be any compositions to which receptor can be bound, which is readily separated from soluble material, and which is otherwise compatible with the overall method of measuring alloantigen. The surface of such supports may be solid or porous and of any convenient shape. Examples of suitable insoluble supports to which the receptor is bound include beads, membranes and microtiter plates. These are typically made of glass, plastic (e.g. polystyrene), polysacharides, nylon or nitrocellulose. Microtiter plates are especially convenient because a large number of assays can be carried out simultaneously, using small amounts of reagents and samples. Where separations are made by magnetism, the support generally includes paramagnetic components, preferably surrounded by plastic.

Before adding samples or fractions thereof, the non-specific binding sites on the insoluble support i.e. those not occupied by receptor antibody, are generally blocked. Preferred blocking agents include non-interfering proteins such as bovine serum albumin, casein, gelatin, and the like. Alternatively, several detergents at non-interfering concentrations, such as Tween, NP40, TX100, and the like may be used.

Samples, fractions or aliquots thereof are then added to separately assayable supports (for example, separate wells of a microtiter plate) containing support-bound alloantigen specific receptors. Preferably, a series of standards, containing known concentrations of soluble alloantigen is assayed in parallel with the samples or aliquots thereof to serve as controls. As disclosed above, samples may be preincubated with added alloantigen, alloantigen-specific ligand, or other additives to effect complex formation. In an example of HLA typing, a series of defined HLA-specific ligands (preferably antibodies) are added to separate sample aliquots that are assayed in parallel for the presence of respective HLA. In another example of PRA, a series of defined HLAs are added to separate sample aliquots that are then assayed in parallel for the presence of respective HLA-specific ligands (generally antibodies).

In one embodiment of the invention, assayed samples include: first and second samples from different sources and a mixture, or aliquot thereof, of those first and second samples. The mixture of the first and second samples may be of any useful ratio; preferably between 1:1 and 1:100 or 100:1; more preferably 1:1. The mixture may be preincubated before addition to the wells, to increase alloantigen-specific ligand binding to alloantigen.

In another embodiment of the invention, the targeted class(es) of ligands (including alloantigen-specific ligands complexed with alloantigen) are at least partially separated from uncomplexed alloantigen in a sample. The separation may be accomplished by selective precipitation or selective adsorption from the sample of either the complexed or uncomplexed alloantigen. The assayed samples then include the resultant fraction: supernatant or pellet, solid or liquid phase; that preferentially contains ligand including ligand complexed with alloantigen. This embodiment is also applicable to comparisons of alloantigen immune complex formation in fluids derived from graft recipients before and after grafting.

Generally from about 0.001 to 1 ml of sample, diluted or otherwise, is sufficient, usually about 0.01 ml sufficing. Preferably, each sample and standard will be added to multiple wells so that mean values can be obtained for each. The incubation time should be sufficient for soluble alloantigen molecules to bind the insoluble receptors. Generally, from about 0.1 to 3 hr is sufficient, usually 1 hr sufficing.

The invention may be used with or without standards as references. Where used, standards preferably contain soluble alloantigen of known concentration. Examples of suitable HLA antigen standards include B7, A2, and the like. The concentration ranges of the standards will provide references for at least the range of values expected from the test samples. This concentration range will depend upon the assay used to measure alloantigen concentration. In general the range is found between about 1 ng/ml and 1 mg/ml, preferably between 1 and 1000 ng/ml, more preferably between 5 and 500 ng/ml.

After incubation, the insoluble support is generally washed of non-bound components. Generally, a dilute non-ionic detergent medium at an appropriate pH, generally 7-8, is used as a wash medium. From one to six washes may be employed, with sufficient volume to thoroughly wash non-specifically bound proteins present in the sample.

After washing, a solution containing alloantigen specific second receptor is applied. Like the first receptor (discussed supra), the soluble second receptor may be any compound which binds the alloantigen with sufficient specificity such that the receptor-bound alloantigen can be distinguished from other components present on the insoluble support or in the surrounding solution at the time the second receptor is added. Generally, the criteria that apply to selecting first receptors also apply to selecting second receptors. In a preferred embodiment, second receptors are antibodies specific for the same HLA molecules as the first receptors, or a subset thereof. Where monoclonal second receptor antibodies are used, they are preferably directed to a different epitope than that of the first receptors.

Second receptors may be labelled to facilitate direct, or indirect quantification of binding. Examples of labels which permit direct measurement of second receptor binding include radiolabels, such as $^3H$ or $^{125}I$, fluorescers, dyes, beads, chemilumninescers, colloidal particles, and the like. Examples of labels which permit indirect measurement of binding include enzymes where the substrate may provide for a colored or fluorescent product. In a preferred embodiment, the second receptors are antibodies, preferably labeled with a covalently bound enzyme capable of providing a detectable product signal after addition of suitable substrate. Examples of suitable enzymes for use in conjugates include horseradish peroxidase, alkaline phosphatase, malate dehydrogenase and the like. Where not commercially available, such antibody-enzyme conjugates are readily produced by techniques known to those skilled in the art.

Alternatively, the second receptor may be unlabeled. In this case, a labeled second receptor-specific compound is employed which binds to the bound second receptor. Such a second receptor-specific compound can be labelled in any of the above manners. It is possible to select such compounds such that multiple compounds bind each molecule of bound second receptor. Examples of second receptor/second receptor-specific molecule pairs include antibody/anti-antibody and avidin (or streptavidin)/biotin. Since the resultant signal is thus amplified, this technique may be advantageous where only a small amount of alloantigen is present. An example is the use of a labeled antibody specific to the second receptor. More specifically, where the second receptor is a rabbit anti-allotypic antibody, an antibody directed against the constant region of rabbit antibodies provides a suitable second receptor specific molecule. The anti-immunoglobulin will usually come from any source other than human, such as ovine, rodentia, particularly mouse, or bovine.

The volume, composition and concentration of second receptor solution provides for measurable binding to the alloantigen already bound to receptor. Generally, the same volume as that of the sample is used: from about 0.001 to 1 ml is sufficient, usually about 0.1 ml sufficing. The concentration will generally be sufficient to saturate all alloantigen potentially bound to insoluble receptor. When antibody ligands are used, the concentration generally will be about 0.1 to 50 $\mu$g/ml, preferably about 1 $\mu$g/ml. The solution containing the second receptor is generally buffered in the range of about pH 6.5–9.5. The solution may also contain an innocuous protein as previously described. The incubation time should be sufficient for the labeled ligand to bind available bound HLA molecules. Generally, from about 0.1 to 3 hr is sufficient, usually 1 hr sufficing.

After the second receptor or second receptor-conjugate has bound, the insoluble support is generally again washed free of non-specifically bound second receptor, essentially as described for prior washes. After non-specifically bound material has been cleared, the signal produced by the bound conjugate is detected by conventional means. Where an enzyme conjugate is used, an appropriate enzyme substrate is provided so a detectable product is formed. More specifically, where a peroxidase is the selected enzyme conjugate, a preferred substrate combination is $H_2O_2$ and is O-phenylenediamine which yields a colored product under appropriate reaction conditions. Appropriate substrates for other enzyme conjugates such as those disclosed above are known to those skilled in the art. Suitable reaction conditions as well as means for detecting the various useful conjugates or their products are also known to those skilled in the art. For the product of the substrate O-phenylenediamine for example, light absorbance at 490–495 nm is conveniently measured with a spectrophotometer.

In those embodiments of the invention where a mixture of a first and second sample or fraction thereof is assayed, the expected concentration of the mixture is determined from the measured concentrations of each of the two samples multiplied by the respective fraction of the mixture the respective sample comprised. Where the mixture is a 1:1 combination of the two samples, the expected mixture concentration is the sum of one half the concentration of each sample.

Alternatively, the amount of alloantigen in a sample before and after precipitation are compared, e.g. in the case of detection of immune complexes following grafting or transplantation. In a preferred embodiment, the amount of alloantigen in the separated fraction, e.g. precipitate, is expressed as a ratio with that of the sample before fractionation, e.g. precipitation. The invention also finds use in monitoring graft recipients over time since varying amounts of soluble alloantigen are released by the graft and various amounts of antibodies are formed against the graft-released alloantigens, resulting in varying amounts of immune complexes. A follow-up of the amount of precipitable alloantigen may be of value in the diagnosis of graft rejection.

Additionally, kinetic studies—where alloantigen immune complexes are assayed before the sample has reached chemical equilibrium—may be performed to more specifically determine the nature of the alloantigen and immune complexes present in a sample. Kinetic studies are also useful, for example, for simultaneously typing a sample for a plurality of HLA types. Another application of kinetic studies is in situations where precipitated immune complexes are dissociated. For example, the second receptor employed may be partially sterically hindered in its ability to bind the alloantigen while in immune-complexes. In such cases, disassociation may be achieved by, for example, temporarily altering the ionic strength or pH of the solution. A specific example is the use of glycine to lower the pH to 2.5. Thereafter the prior ionic strength or pH is restored and the solution is presented to the second receptor. Accordingly, the second receptor is afforded an opportunity to compete for the binding of uncomplexed alloantigen.

The invention can be practiced qualitatively or quantitatively. In a qualitative assay, the alloantigen concentrations of the samples, mixtures, or fractions thereof are defined relative to one another or to the concentrations of other unstandardized alloantigen samples. In a quantitative assay, all alloantigen concentrations are related to a series of standards of known concentration. Accordingly, absolute (weight/volume) concentration values can be obtained.

To accurately quantify the data, the series of standards generally fall within a range limitation imposed by the method of measurement. For example, in the horseradish peroxidase-O-phenylenediamine assay described above, concentration is related to absorbance at 490–495 nm. This assay generally provides valid measurements if the most concentrated standard yields between 1.0 and 2.0 absorbance units and if the difference between the absorbance value for the most and least concentrated standard is at least 0.4, more preferably at least 0.8 absorbance units.

For quantitative assays, the absorbance value for each standard may be plotted against the soluble alloantigen concentrations on semi-log graph paper and a standard curve constructed with absorbance on the linear y axis and soluble alloantigen concentration (ng/ml) on the logarithmic x axis. The soluble alloantigen concentrations of the individual samples (usually diluted) and the mixture (usually diluted) may then be read off the plot.

In those embodiments involving mixtures of samples, where the expected alloantigen concentration of the mixture differs significantly from the measured concentration, the presence of alloantigen immune complexes is indicated. What difference is significant depends on the precision of the assay used, the amount of alloantigen measured, the number of multiple wells treated for repeat values, and the number of independent assays run. A variety of significance limits for the divergence of the measured value may be set. Examples include where the measured value differs from the mean average by more than two standard deviations of the mean average or where the ratio of the expected to measured value of the mixture is greater than 1.1 or less than 0.9.

A device which may find application with the subject invention is one having a porous substrate to which the receptor specific for the allotypic antigen is bound. Supporting the substrate is an absorbent layer which will absorb the various fluids, including samples and washes. Desirably, the absorbent layer and porous layer are separated by a flow control film, having a plurality of orifices which direct the rate and direction of flow through the porous layer. For further description of this device, see U.S. application Ser. No. 444,814, filed Dec. 1, 1989 and now abandoned. This device, as well as comparable devices allow for the simultaneous determination of a plurality of samples, either from different sources, or at different concentrations from the same source. Thus, one can carry out a plurality of determinations at the same time. Alternatively, microtiter plates may be employed where the bottoms of the wells are porous to allow for filtration. The particular device which is employed will depend upon the number of samples to be determined, available equipment, and the like.

The following examples are offered by way of illustration and not by way of limitation.

EXAMPLE I: INTERFERENCE IMMUNOASSAY

Wells of microtiter strips (12×8 well strips, Nunc) were coated with a monomorphic anti-sHLA class I monoclonal antibody specific to HLA B7 and B27 (coating time 1 hr, at 25° C. with 1 µg/ml antibody in 0.1 M PBS pH 7.4, 100 µl per well), followed by blocking with 0.1 M PBS pH 7.4 containing 1% casein w/v. Nine parallel wells were then incubated with 100 µl of respectively, five different concentrations of standard (prepared by diluting HLA B7 to 6, 25, 62, 125 and 210 ng/ml in 0.1 M PBS, pH 7.4. described below), 1/25 dilution of serum from 18 HLA B7 positive individuals (as phenotyped by microlymphocytotoxicity), 7 HLA B7, B27 positive individuals, 13 HLA B27 positive individuals, and 7 HLA B7 negative, B27 negative individuals. All samples were tested in the described sandwich ELISA with and without a prior incubation with 1 µg/ml of an anti-B7 monoclonal antibody (which does not crossreact with HLA-B27. The Absorbance (described below) was compared with and without the antibody pretreatment for each sample. After 30 min., the wells were washed three times with 250 µl per well of PBS with 0.1% Tween-20. To all wells were then added 100 µl of an anti-β-2-microglobulin monoclonal antibody conjugated to horseradish peroxidase (incubation time 30 min, at 25° C. with 1 µg/ml antibody in 0.1 M PBS pH 7.4, 100 µl per well). After washing three times as described above, 100 µl of o-phenylenediamine (10 mg/ml in citrate buffer pH 5 with hydrogen peroxide) substrate solution was added to each well and incubated in the dark, at room temperature, for 15 min. Color development was measured using a spectrophotometer at 495 nm.

These assay conditions provide valid measurements if the 210 ng/ml standard yields an absorbance reading between 1.0 and 2.0 and if the difference between the absorbance value for the 210 ng/ml standard and the 6 ng/ml standard is at least 0.8 absorbance units. The absorbance value for each standard was plotted against the sHLA concentrations on semi-log graph paper and a standard curve was constructed with absorbance on the linear y axis and HLA concentration (ng/ml) on the logarithmic x axis. The sHLA concentrations of the individual samples and the mixture were then read off the plot and the measured concentration of the mixture compared to the expected concentration, i.e. half the sum of the concentrations of the two individual samples.

The ratio (defined as the HLA concentration in the presence of anti-B7 monoclonal antibody divided by the concentration without the antibody) range of the HLA B7 positive samples was 1.7–4.2; with the HLA B7, B27 positive samples, the range was 0.9–2.1. In contrast, the ratio range for the HLA B27 positive samples was 0.9–1.2 and for the HLA B7 negative, B27 negative samples the range was 0.9–1.0.

EXAMPLE II: COMPARATIVE PRECIPITATION

In the following exemplification of the "Comparative Precipitation Assay" embodiment of the invention, the first sample was a supernatant from a transfected cell line (C1R neo B7) which secretes HLA B7. The HLA concentration of the supernatant was found to be approx. 1 µg/ml. The second samples are a series of alloantisera with antibodies to HLA-B7 (as tested by microlymphocytotoxicity) or normal serum samples of male blood donors. Mixtures of the first and second sample (1:1) were incubated for 15 minutes.

One ml of polyethylene glycol 8000 was added to each sample to reach a final concentration of 12.5% (w/vol). The samples were incubated in parallel for 10 min, centrifuged at 12,000 x g for 15 min., and the supernatants aspirated. Each pellet was then resuspended in a buffer protein solution (PBS 0.1 M, pH 7.4, 1% casein (w/vol)), vortexed, and the resultant solution assayed by the ELISA essentially as described in the preceding example.

The ratio of HLA Absorbance (O.D.) in the mixture divided by HLA O.D in the first plus a second sample was determined. Four samples with anti-HLA B7 antibodies showed ratios ranging from 3.10 to 21.26. Thirteen control samples showed O.D. in the mixture below the measuring range of the ELISA and yielded ratios <1.77.

The subject methods provide substantial improvements over what has been previously available. More specifically, the identification of allotypic cross-reactivity by identifying alloantigen-specific ligand in separated complexes or by the interference immunoassay disclosed herein provides an alternative approach to allotypic characterizations than other approaches such as directly assaying for the presence of allotypic antibodies. The disclosed methods are easy to use, rapid, and do not require cells. The method is adaptable, so that it can be HLA (class, locus, or allele) specific. The method can be used before transplantation and be used for graft rejection monitoring after transplantation. It avoids many of the pitfalls of the presently available methods in its simplicity, rapidity, lack of requirement for cells and objective determination.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for detecting in a sample of a mixture of antibodies, an antibody that reacts with a selected soluble HLA antigen, said method comprising:

separating from said sample a fraction comprising a portion of said antibodies, by means of adding a soluble immune complex precipitating agent to form a precipitate in said sample, said fraction being substantially free of the selected HLA antigen unassociated with antibody; and, detecting the presence of said selected HLA antigen in said fraction;

wherein said presence of said selected HLA antigen correlates with the presence in said sample of said antibody which reacts with said selected HLA antigen.

2. The method of claim 1, wherein said sample is a blood sample.

3. The method of claim 2, wherein said blood sample is serum.

4. The method of claim 1, wherein said detecting is accomplished by immunoassay.

5. A method for detecting lack of histocompatibility by detecting in a blood sample of a mixture of antibodies, an antibody that reacts with a selected soluble HLA antigen, wherein said sample is from an intended transplant organ recipient, said method comprising:

combining said recipient blood sample with a blood sample from a prospective transplant organ donor;

adding a soluble immune complex precipitating agent to form a precipitate; and detecting the presence of said soluble HLA antigen in said precipitate;

wherein said presence of said soluble HLA antigen correlates with the lack of histocompatibility of said recipient with said prospective transplant organ donor.

* * * * *